United States Patent [19]

Terada et al.

[11] 4,161,538

[45] Jul. 17, 1979

[54] SUBSTITUTED PHENYLACETIC ACID DERIVATIVES AND PROCESS FOR THE PREPARATION THEREOF

[75] Inventors: Atsusuke Terada; Kazuyuki Wachi; Eiichi Misaka, all of Hiromachi, Japan

[73] Assignee: Sankyo Company Limited, Tokyo, Japan

[21] Appl. No.: 885,527

[22] Filed: Mar. 10, 1978

[30] Foreign Application Priority Data

Apr. 5, 1977 [JP]  Japan .................................. 52-38906
Apr. 5, 1977 [JP]  Japan .................................. 52-38907
Jun. 10, 1977 [JP]  Japan .................................. 52-68468

[51] Int. Cl.$^2$ ........................ A61K 31/19; C07C 65/20
[52] U.S. Cl. ............................... 424/317; 260/501.11; 260/448 R; 424/316; 424/319; 424/267; 424/248.55; 544/107; 562/440; 562/459; 546/239
[58] Field of Search ............................... 562/459, 440; 260/501.11, 448 R, 293.78, 293.8; 424/316, 317, 319, 267, 248; 544/107

[56] References Cited

U.S. PATENT DOCUMENTS

| | | | |
|---|---|---|---|
| 3,825,587 | 7/1974 | Diamond et al. | 562/440 |
| 3,864,384 | 2/1975 | Diamond et al. | 562/440 |
| 3,894,080 | 7/1975 | Diamond et al. | 562/459 |
| 4,008,269 | 2/1977 | Diamond et al. | 562/459 |
| 4,031,133 | 6/1977 | Maillard | 562/459 |

OTHER PUBLICATIONS

Maillard, Chemical Abstracts, 83, 43056(d), 1975.
Maillard, Chemical Abstracts, 78, 147578(p), 1973.

*Primary Examiner*—James O. Thomas, Jr.
*Assistant Examiner*—G. T. Breitenstein
*Attorney, Agent, or Firm*—Flynn & Frishauf

[57] ABSTRACT

4-(2-Oxo- or hydroxyimino-cycloalkan-1-ylmethyl)-phenylacetic acid derivative and nontoxic pharmaceutically acceptable salt thereof are useful as an anti-inflammatory agent. The above 2-oxo-compound may be prepared by (a) hydrolyzing and decarboxylating 4-(1-alkoxycarbonyl-2-oxocycloalkan-1-ylmethyl)phenylacetic acid ester derivative or (b) reacting p-halomethyl-phenylacetic acid ester derivative with an enamine of cycloalkanone and hydrolyzing the resulting product. And further, the above 2-hydroxyimino-compound may be prepared by (c) reacting 4-(2-oxocycloalkan-1-ylmethyl)phenylacetic acid derivative (the product of process (a) or (b)) with hydroxylamine or (d) reacting a dilithium salt of cycloalkanone oxime with p-halomethyl- or p-sulfonyloxymethyl-phenylacetic acid ester derivative and hydrolyzing the resulting product.

32 Claims, No Drawings

SUBSTITUTED PHENYLACETIC ACID DERIVATIVES AND PROCESS FOR THE PREPARATION THEREOF

The present invention relates to novel substituted phenylacetic acid derivatives that are useful as anti-inflammatory agents and processes for the preparation thereof.

More particularly, this invention relates to novel substituted phenylacetic acid derivatives having the formula

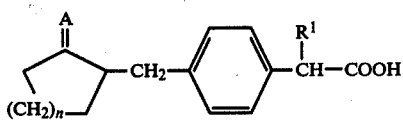

wherein $R^1$ represents hydrogen atom or a lower alkyl group, A represents oxo group or hydroxyimino group, n is an integer from 1 to 3 and the nontoxic pharmaceutically acceptable salts thereof.

In the above-mentioned formula (I), $R^1$ is preferably hydrogen atom, or a straight- or branched-chain alkyl group having 1 to 4 carbon atoms such as methyl, ethyl, n-propyl, isopropyl, n-butyl and isobutyl. More preferred compounds are those in which $R^1$ is hydrogen atom or methyl group and n is 1 or 2. The most preferred compounds are those in which $R^1$ is methyl group and n is 1 or 2.

The substituted phenylacetic acid derivatives having the formula (I) may be converted into the pharmaceutically acceptable salts. The pharmaceutically acceptable salts include the salt of alkali metal or alkaline earth metal such as sodium or calcium; the aluminum salt; the ammonium salt; the salt of organic base such as triethylamine, dicyclohexylamine, dibenzylamine, morpholine, piperidine or N-ethylpiperidine; or the salt of basic amino acid such as lysine or arginine.

Due to the presence of asymmetric carbon atom(s), there exist optical isomers in the compound having the formula (I). When, accordingly, the compound having the formula (I) is obtained as a mixture of the optical isomers, each of the isomers can be individually obtained by utilizing conventional optical resolution techniques. And further, due to the presence of a hydroxyimino group, there exist geometrically isomeric syn and anti forms in the compound having the formula (I) wherein A represents hydroxyimino group. When, accordingly, the compound having the formula (I) is obtained as a mixture of these isomers, each of the isomers can be individually obtained by utilizing conventional separation techniques. In the compound having the formula (I), its optical isomers, geometrical isomers as well as their mixture are all represented by a single structural formula, but the scope of the present invention is by no means limited thereby.

As a result of extensive studies on the synthesis and pharmacological activities of substituted phenylacetic acid derivatives for the purpose of developing an anti-inflammatory agent, we have found that a novel substituted phenylacetic acid derivative having the above-mentioned formula (I) exhibits excellent anti-inflammatory, analgesic and antipyretic activities.

It is, accordingly, a primary object of the present invention to provide a new class of substituted phenylacetic acid derivatives which has a utility as anti-inflammatory, analgesic and antipyretic agents.

It is another object of this invention to provide processes for the preparation of such substituted phenylacetic acid derivatives.

The following compounds may be mentioned as examples of the compounds prepared according to the present invention.

(1) 2-[4-(2-Oxocyclopentan-1-ylmethyl)phenyl]-propionic acid
(2) 4-(2-Oxocyclopentan-1-ylmethyl)phenylacetic acid
(3) 2-[4-(2-Oxocyclohexan-1-ylmethyl)phenyl]propionic acid
(4) 4-(2-Oxocyclohexan-1-ylmethyl)phenylacetic acid
(5) 2-[4-(2-Oxocycloheptan-1-ylmethyl)phenyl]propionic acid
(6) 2-[4-(2-Oxocyclopentan-1-ylmethyl)phenyl]propionic acid L-arginine salt
(7) 4-(2-Oxocyclohexan-1-ylmethyl)phenylacetic acid L-lysine salt
(8) 2-[4-(2-Hydroxyiminocyclopentan-1-ylmethyl)-phenyl]-propionic acid
(9) 4-(2-Hydroxyiminocyclopentan-1-ylmethyl)-phenylacetic acid
(10) 2-[4-(2-Hydroxyiminocyclohexan-1-ylmethyl)-phenyl]-propionic acid
(11) 4-(2-Hydroxyiminocyclohexan-1-ylmethyl)-phenylacetic acid
(12) 2-[4-(2-Hydroxyiminocycloheptan-1-ylmethyl)-phenyl]-propionic acid
(13) 2-[4-(2-Hydroxyiminocyclopentan-1-ylmethyl)-phenyl]-propionic acid L-arginine salt
(14) 4-(2-Hydroxyiminocyclohexan-1-ylmethyl)-phenylacetic acid L-lysine salt According to the present invention, the compounds of the above-mentioned formula (I) can be obtained by the following processes.

Process I

A compound having the above-mentioned formula (I) wherein A represents oxo group, namely, a compound having the formula

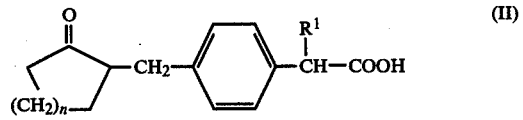

wherein $R^1$ and n have the same meanings as defined above can be obtained by hydrolyzing a keto dicarboxylic acid ester derivative having the formula

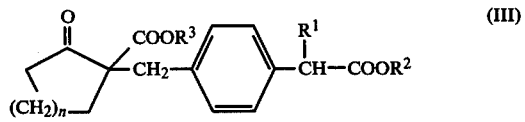

wherein $R^1$ and n have the same meanings as defined above, and $R^2$ and $R^3$ represent a lower alkyl group such as methyl, ethyl, n-propyl or isopropyl group, followed by subjecting to decarboxylating reaction.

In carrying out the above-described process, the first step of hydrolyzing reaction is performed by contacting the compound having the formula (III) with an acid or a base as a hydrolyzing agent.

As the acid or base to be employed may be used without any limitation those which are usually employed for a hydrolyzing reaction, but a mineral acid such as hydrochloric acid, hydrobromic acid, sulfuric acid and the like, or an alkali metal hydroxide such as sodium hydroxide, potassium hydroxide and the like may be mentioned as a preferable acid or base. The reaction is usually carried out in the presence of a solvent, and the solvent preferably employed is water; an organic solvent, for example, an alcohol such as methanol, ethanol or n-propanol, a glycol such as ethylene glycol or diethylene glycol, an aliphatic carboxylic acid dialkyl amide such as dimethyl formamide or dimethyl acetamide; or a mixture of these organic solvents and water. As to the reaction temperature there is no particular limitation, but a range of from room temperature to 150° C. is usually used. The reaction time is varied mainly depending upon the reaction temperature, the hydrolyzing agent employed and the like, but it usually takes about 1 to 12 hours.

After the reaction is completed, the desired hydrolyzed product can be recovered from the reaction mixture by a conventional method. When, for example, a base is employed as a hydrolyzing agent, the reaction mixture is washed with an organic solvent like ether, the aqueous layer is acidified by addition of an acid like hydrochloric acid, and then extracted with an organic solvent like ether. The extract is washed with water, dried, and the solvent is removed by distillation to afford the desired product. The acidified aqueous suspension, however, may be subjected directly to the subsequent decarboxylating reaction.

The second step of decarboxylating reaction of the hydrolyzed product thus obtained may be carried out by heating in the presence or absence of a solvent.

In the case of heating in the presence of a solvent may be employed water; an organic solvent, for example, an aromatic hydrocarbon such a benzene, toluene, xylene, cymene and the like, an ether such as dioxane; or a mixture of these organic solvents and water preferably in the presence of an acid such as hydrochloric acid, p-toluene sulfonic acid and the like.

In the case of heating in the absence of a solvent, the reaction is desired to be performed under reduced pressure in an atmosphere of an inert gas such as nitrogen in order to prevent the side reaction to occur.

The heating temperature for the reaction is preferably from about 50° to 200° C., and the reaction time is varied mainly depending upon the sort of the starting compound, the reaction temperature and the like, but it takes usually about 15 minutes to 3 hours.

When an acid is employed in the hydrolyzing reaction according to the method of the invention, the decarboxylating reaction can also be performed at the same time. For this purpose, the reaction is preferably carried out by heating the ester compound having the formula (III) in an ether such as dioxane in the presence of a mineral acid such as hydrochloric acid, hydrobromic acid, sulfuric acid and the like. The reaction is performed usually at the temperature of 100° to 150° C., preferably at the reflux temperature of the solvent employed. The reaction time is about 1 to 20 hours.

After completion of the reaction, the desired compound having the formula (II) can be recovered by a conventional method. For example, the reaction mixture is extracted with a suitable organic solvent, the organic layer thus obtained is washed with water and dried, and the desired product is then obtained by removing the solvent by distillation from the extract.

The desired compound thus obtained, if necessary, may be further purified by a usual technique such as, for example, a vacuum distillation, a column chromatography or a recrystallization method, and may be converted into a form of the aforementioned pharmaceutically acceptable salt by a conventional procedure.

In carrying out the process according to the present invention, the novel compound having the abovementioned formula (III) which is employed as the starting compound can be prepared, for example, by the following reaction.

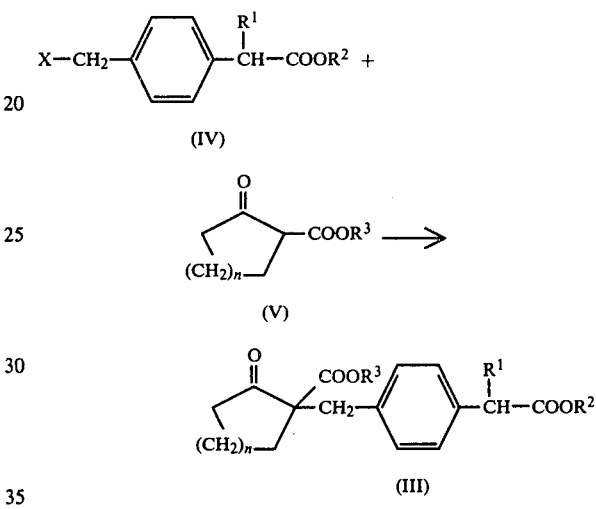

In the above formulas, $R^1$, $R^2$, $R^3$ and n have the same meanings as defined above and X represents a halogen atom such as chlorine or bromine.

Namely, the reaction for preparing the compound having the formula (III) is carried out by reacting a benzyl halide derivative having the formula (IV) with a cycloalkanone carboxylic acid ester derivative having the formula (V) in the presence of a base.

As the base to be employed may be used without any particular limitation those which are usually employed for an alkylating reaction of an active methylene group, but preferable bases may be, for example, an alkali metal alkoxide such as sodium methoxide, sodium ethoxide, potassium tert-butoxide and the like, an alkali metal amide such as sodium amide, potassium amide and the like, or an alkali metal hydride such as sodium hydride, potassium hydride and the like. The reaction is preferably performed in the presence of a solvent, and the solvent to be preferably employed is, for example, an alcohol such as methanol, ethanol, tert-butanol and the like, an aliphatic carboxylic acid dialkyl amide such as dimethyl formamide, dimethyl sulfoxide, an ether such as tetrahydrofuran, dioxane, 1,2-dimethoxyethane and the like. As to the reaction temperature there is not any particular limitation, but a range of from room temperature to the reflux temperature of the solvent is usually employed. The reaction time is varied depending upon the sort of the base to be used, the reaction temperature and the like, but it usually takes from 1 to 5 hours.

After the reaction is completed, the desired compound having the formula (III) can be recovered by treating the reaction mixture according to a conventional method, and the compound thus obtained, if necessary, may be further purified by a usual manner such as, for example, a vacuum distillation, a column chromatography and the like method.

Process 2

A compound having the above-mentioned formula (I) wherein A represents oxo group, namely, a compound having the formula

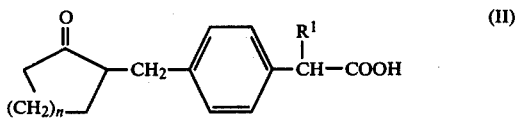 (II)

wherein $R^1$ and n have the same meanings as defined above can be obtained by reacting a benzyl halide derivative having the above-mentioned formula

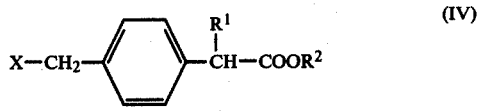 (IV)

wherein $R^1$, $R^2$ and X have the same meanings as defined above with an enamine derivative having the general formula

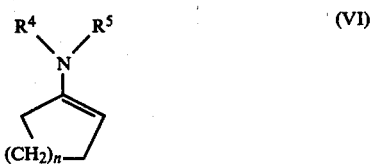 (VI)

wherein $R^4$ and $R^5$ taken individually represent a lower alkyl group such as methyl, ethyl, n-propyl, isopropyl, n-butyl or isobutyl group, or taken jointly together with the adjacent nitrogen atom comprise a residue of a cyclic amine which may optionally involve an oxygen atom, such as 1-pyrrolidinyl, piperidino, morpholino and the like residue, and n has the same meaning as defined above and hydrolyzing the compound thus preprared having the formula

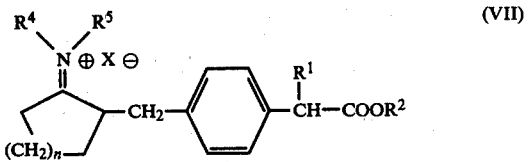 (VII)

wherein $R^1$, $R^2$, $R^4$, $R^5$, X and n have the same meanings as defined above.

In carrying out the above-described process, the first reaction by which a halide compound (IV) and an enamine compound (VI) are condensed is performed by heating in the presence of a solvent.

As the preferable solvent to be employed may be mentioned an aromatic hydrocarbon such as benzene, toluene, xylene and the like, or an ether such as dioxane, and the reaction may be carried out at the temperature of about 80° to 140° C., preferably at the reflux temperature of the solvent employed. The reaction time is varied depending upon the reaction temperature and the like, but it usually takes 1 to 30 hours.

The subsequent hydrolyzing reaction may be carried out using a residue which is obtained according to a usual manner by removing the solvent from the reaction mixture after completion of the reaction. The said hydrolyzing reaction may be carried out by contacting the compound having the formula (VII) thus obtained with an acid or a base as a hydrolyzing agent.

As the acid or base to be employed may be used without any limitation those which are usually employed for a hydrolyzing reaction, but a mineral acid such as hydrochloric acid, hydrobromic acid, sulfuric acid and the like, or an alkali metal hydroxide such as sodium hydroxide, potassium hydroxide and the like may be mentioned as a preferable acid or base. The reaction is usually carried out in the presence of a solvent, and the solvent preferably empolyed is water; an organic solvent, for example, an alcohol such as methanol, ethanol or n-propanol, a glycol such as ethylene glycol or diethylene glycol; or a mixture of these organic solvents and water. As to the reaction temperature there is no particular limitation, but a range of from room temperature to about 110° C. is usually employed. The reaction time is varied mainly depending upon the reaction temperature, the hydrolyzing agent used and the like, but it usually takes about 10 minutes to 6 hours.

After the reaction is completed, the desired compound having the formula (II) can be recovered from the reaction mixture by a conventional method, for example, by a similar method described earlier in the hydrolyzing reaction of the Process 1.

The desired compound thus prepared may be further purified, if necessary, by a usual technique such as, for example, by a vacuum distillation, a column chromatography or a recrystallization method, and may also be converted into a form of the aforementioned pharmaceutically acceptable salt by a conventional procedure.

Process 3

A compound having the above-mentioned formula (I) wherein A represents hydroxyimino group, namely, a compound having the formula

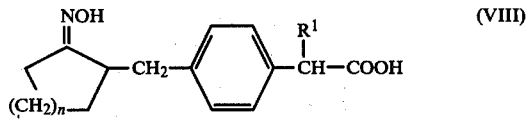 (VIII)

wherein $R^1$ and n have the same meanings as defined above can be obtained by reacting a keto carboxylic acid derivative having the above-mentioned formula which is prepared in the Process 1 or 2

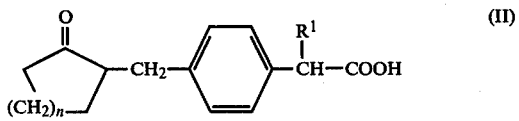 (II)

wherein $R^1$ and n have the same meanings as defined above with hydroxylamine or with a salt of hydroxylamine in the presence of a base.

In carrying out the above-described process, the salt of hydroxylamine to be preferably employed is that of a mineral acid such as hydrochloric acid salt, sulfuric acid salt and the like, and the base to be preferably employed is an alkali metal hydroxide such as sodium hydroxide, potassium hydroxide and the like, an alkali metal or an alkaline earth metal salt of acetic acid such as sodium acetate, potassium acetate, calcium acetate and the like, or an alkali metal alcoholate such as sodium methoxide, sodium ethoxide, potassium tert-butoxide and the like. The reaction is preferably carried out using a base and a salt of hydroxylamine usually in the presence of a solvent, and the solvent preferably employed is water; an alcohol such as methanol, ethanol, tert-butanol and the like; an aliphatic carboxylic acid dialkylamide such as dimethyl formamide, dimethyl acetamide and the like; dimethyl sulfoxide; an ether such as tetrahydrofuran, dioxane, 1,2-dimethoxyethane and the like; or an aromatic hydrocarbon such as benzene, toluene and the like. As to the reaction temperature there is no particular limitation, but a range of from room temperature to 100° C. is preferably employed. The reaction time is varied depending upon the sort of base to be employed, the reaction temperature and the like, but it usually takes 30 minutes to 10 hours.

After the reaction is completed, the desired compound having the formula (VIII) can be recovered from the reaction mixture by a conventional method. For example, the reaction mixture is poured into ice-water, the mixture is acidified by addition of an acid like hydrochloric acid, and extracted with a suitable organic solvent. The extract is washed with water, dried, and the desired compound is then obtained by evaporating the solvent from the extract.

The desired compound thus obtained, if necessary, may be further purified by a usual manner such as, for example, a recrystallization method, a column chromatography and the like method, and may also be converted into a form of the aforementioned pharmaceutically acceptable salt by a conventional procedure.

Process 4

A compound having the above-mentioned formula (I) wherein A represents hydroxyimino group, namely, a compound having the formula

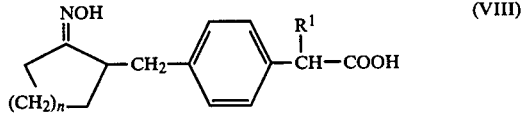

(VIII)

wherein $R^1$ and n have the same meanings as defined above can be obtained by reacting a cycloalkanone oxime having the formula

(IX)

wherein n has the same meaning as defined above with an organolithium compound and reacting the resulting dilithium hydroxyimino compound with a phenylacetic acid ester derivative having the formula

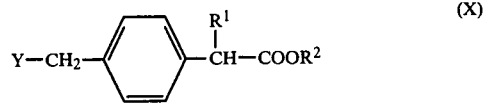

(X)

wherein $R^1$ and $R^2$ have the same meanings as defined above, and Y represents a halogen atom such as bromine or iodine, or a residue of a sulfonic acid such as methanesulfonyloxy, benzenesulfonyloxy or p-toluenesulfonyloxy group, followed by hydrolyzing the thus formed hydroxyimino-substituted phenylacetic acid ester derivative having the formula

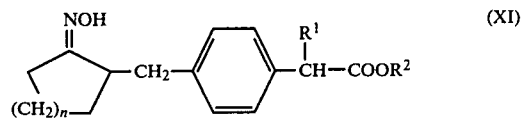

(XI)

wherein $R^1$, $R^2$ and n have the same meanings as defined above.

In carrying out the above process, the organolithium compound to be preferably employed for reacting an oxime compound (IX) is a lower alkyl lithium compound such as methyllithium, n-butyllithium, sec-butyllithium or tert-butyllithium, and the amount to be used is usually in two molar ratio to an oxime compound (IX). The reaction is preferably carried out in the presence of a solvent, and the solvent to be preferably used is an ether such as ethyl ether, tetrahydrofuran, dimethoxymethane, 1,2-dimethoxyethane, diglyme, triglyme and the like. As to the reaction temperature there is no particular limitation, but a range of from 0° to 50° C. is preferably employed. The reaction time is varied depending upon the sort of the starting compound (X), the reaction temperature and the like, but it usually is enough to be 10 minutes to 1 hour.

After the reaction is completed, the compound having the above-mentioned formula (XI) can be recovered from the reaction mixture by a conventional manner. For example, the reaction mixture is poured into a mixture of ice-water and concentrated hydrochloric acid, and extracted with an organic solvent like ether. The extract is washed with water, dried, and the desired compound is then obtained by evaporating the solvent from the extract.

The compound (XI) thus obtained, if necessary, may be further purified by a usual method such as, for example, a recrystallization method, a column chromatography and the like method, but may be directly used as the starting compound for the subsequent hydrolyzing reaction.

The said hydrolyzing reaction of the compound having the formula (XI) is performed by contacting it with an acid or a base as a hydrolyzing agent.

As the acid or base to be employed may be used those which are usually employed for a hydrolyzing reaction without any limitation, but a mineral acid such as hydrochloric acid, hydrobromic acid, sulfuric acid and the like or an alkali metal hydroxide such as sodium hydroxide, potassium hydroxide and the like may be mentioned as a preferable acid or base. The reaction is usually carried out in the presence of a solvent, and the solvent preferably employed is water; an organic solvent, for example, an alcohol such as methanol, ethanol or n-propanol, a glycol such as ethylene glycol or diethylene glycol, an aliphatic carboxylic acid dialkyl amide such as dimethyl formamide or dimethyl acetamide; or a mixture of these organic solvents and water. As to the reaction temperature there is no particular limitation, but a range of from room temperature to 100° C. is usually used. The reaction time is varied mainly depending upon the reaction temperature, the hydrolyzing agent employed and the like, but it usually takes about 1 to 12 hours.

After the reaction is completed, the desired compound having the above-mentioned formula (VIII) can be recovered from the reaction mixture by a conventional manner. When, for example, a base is employed as a hydrolyzing agent, water is added to the reaction mixture, the organic solvent is removed by distillation and the residual layer is acidified by addition of hydrochloric acid. The desired compound may be then obtained either by filtrating the compound precipitated as crystals from the acidified layer, or by extracting the acidified layer with an organic solvent like ether and evaporating the solvent from the water-washed and dried extract.

The desired compound (VIII) thus obtained, if necessary, may be further purified by a usual manner such as for example, a recrystallization method, a column chromatography and the like method, and may also be converted into a form of pharmaceutically acceptable salt according to a usual technique.

The aforementioned reaction proceeds through a path in which a phenylacetic acid ester derivative (X) is reacted with a dilithium hydroxyimino compound represented by the formula

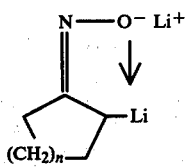   (XII)

wherein n has the same meaning as defined above which is formed from an oxime compound (IX) and an organolithium compound, and therefore, it can be assumed that the so-called syn isomer is stereoselectively prepared as a reaction product. Accordingly, the present Process provides an excellent preparative method characterized in that only syn stereoisomer is formed as the desired compound and further the number of processes is reduced as compared with above-mentioned Process 3.

The substituted phenylacetic acid derivative having the above-mentioned formula (I) according to the present invention exhibits an excellent anti-inflammatory, analgesic and antipyretic activities as shown by the pharmacological tests, and results obtained are described below in the table.

| Medicine | Anti-inflammatory and Analgesic Activities | |
|---|---|---|
| | Inhibition(%) Anti-inflammatory 25 mg/kg (P.O.) | Analgesic 19 mg/kg (P.O.) |
| 2-(4-(2-Oxocyclopentan-1-ylmethyl)phenyl)-propionic acid | 51.4 | 95.8 |
| 4-(2-Oxocyclopentan-1-ylmethyl)phenylacetic acid | 65.6 | 42.5 |
| 2-(4-(2-Oxocyclohexan-1-ylmethyl)phenyl)-propionic acid | 79.9 | 63.3 |
| 4-(2-Oxocyclohexan-1-ylmethyl)phenylacetic acid | 35.1 | 45.1 |
| 2-(4-(2-Oxocyclopentan-1-ylmethyl)phenyl)-propionic acid l-arginine salt | 69.8 | 66.7 |
| 2-(4-(2-Hydroxyiminocyclopentan-1-ylmethyl)phenyl)propionic acid | 67.4 | 70.0 |
| 4-(2-Hydroxyiminocyclopentan-1-ylmethyl)phenylacetic acid (an isomer of m.p. 137°-239° C.) | 49.7 | 54.8 |
| 2-(4-(2-Hydroxyiminocyclohexan-1-ylmethyl)phenyl)propionic acid | 78.2 | 53.1 |
| | 30.6 | 37 |
| Reference Medicine: Phenylbutazone | 57.4 (100 mg/kg) | |

The pharmacological tests were performed according to the following methods.

Anti-inflammatory activity

The carrageenin edema method was employed using Wistar strain rat. [C. A. Winter, E. A. Risley, G. W. Nuss; J. Pharmacol. Exp. Therap., 141, 369(1963)]

Analgesic activity

The thermally induced pain method was employed using Wistar strain rat. [Y. Iizuka, K. Tanaka; Folia Pharmacol. Jap., 70, 697(1974)]

As clearly seen from the above-described results of the pharmacological tests, the compounds having the formula (I) and their pharmaceutically acceptable salts are useful as an analgesic, anti-inflammatory agent. As the administration methods are mentioned, for example, the oral route in the form of tablet, capsule, granule, powder or syrup, and per intestine route in the form of suppository. The dosage unit is varied depending upon the symptoms, age, body weight and the like of the patient, but a usual unit is in amounts of from about 50 mg to 2000 mg per day for the adult, and it may be given once a day or several times separately a day.

Below are given Examples and Referential Examples to further illustrate the present invention.

EXAMPLE 1

2-[4-(2-Oxocyclopentan-1-ylmethyl)phenyl]-propionic Acid

Twenty grams of ethyl 2-[4-(1-ethoxycarbonyl-2-oxocyclopentan-1-ylmethyl)phenyl]propionate was dissolved in 30 ml of dioxane and 100 ml of 47% hydrobromic acid and the solution was refluxed for 6 hours. The reaction mixture was then extracted with ether, the extract was washed with water, dried over anhydrous sodium sulfate, and the solvent removed by distillation to give an yellow oily substance. The product was subjected to a vacuum distillation to yield 13.1 g of the desired compound as a colorless oily substance, b.p. 190°-195° C. at 0.3 mm Hg (bath temp.). The compound solidified as it was cooled to crystals, m.p. 108.5°-111° C.

Elementary analysis for $C_{15}H_{18}O_3$ Calculated: C, 73.14; H, 7.37. Found: C, 73.19; H, 7.28.

EXAMPLE 2

4-(2-Oxocyclopentan-1-ylmethyl)phenylacetic Acid

Into a mixture of 20 ml of 47% hydrobromic acid and 15 ml of dioxane was dissolved 9.2 g of ethyl 4-(1-ethoxycarbonyl-2-oxocyclopentan-1-ylmethyl)phenylacetate and the solution was refluxed for 6 hours. The solvent was then removed by distillation from the reaction mixture, the residue was poured into ice-water and extracted with ether. The extract was washed with water, dried over anhydrous sodium sulfate, the solvent removed by distillation to give an oily substance, which was subjected to a vacuum distillation to yield 6.0 g of an oily product, b.p. 185°–195° C. at 0.7 mm Hg (bath temp.).

Elementary analysis for $C_{14}H_{16}O_3$ Calculated: C, 72.39; H, 6.94. Found: C, 72.08; H, 6.55.

EXAMPLE 3

2-[4-(2-Oxocyclohexan-1-ylmethyl)phenyl]-propionic Acid

Thirteen grams of ethyl 2-[4-(1-ethoxycarbonyl-2-oxocyclohexan-1-ylmethyl)phenyl]propionate was dissolved in 200 ml of 80% ethanol containing 5 g of potassium hydroxide and the solution was refluxed for 2 hours. Ethanol was removed by distillation from the reaction mixture, 100 ml of water was added to the residue and the mixture was extracted with ether. The aqueous layer was heated at 50°–60° C. with stirring for 1 hour after addition of 100 ml of conc. hydrochloric acid, extracted with ether, the extract was washed with water, dried and the solvent removed by distillation to give an yellow oily substance, which was chromatographed on a column of silica gel affording a colorless oily substance from an eluate with a mixture of benzene:ethyl acetate = 5:1. The substance was subjected to a vacuum distillation to give 4.1 g of the desired compound as a colorless oily substance, b.p. 190°–195° C. at 0.4 mm Hg (bath temp.). The compound solidified as it was cooled to crystals, m.p. 84°–86° C.

Elementary analysis for $C_{16}H_{20}O_3$ Calculated: C, 73.82; H, 7.74. Found: C, 73.72; H, 7.58.

EXAMPLE 4

4-(2-Oxocyclohexan-1-ylmethyl)phenylacetic Acid

A mixture of 6.39 g of ethyl p-chloromethylphenylacetate, 4.53 g of 1-pyrrolidinyl-1-cyclohexene and 110 ml of toluene was heated under reflux for 21 hours. After cooling, the solvent was removed by distillation from the reaction mixture, ether and 100 ml of 5% hydrochloric acid were successively added to the residue, the mixture stirred for 1 hour at room temperature, and then extracted with ether. The extract was washed with water, dried over anhydrous sodium sulfate, and the solvent removed by distillation to give an oily substance, which was subjected to a vacuum distillation affording 1.7 g of the ester of the desired compound, b.p. 165°–180° C. at 0.5 mm Hg (bath temp.). The ester compound (1.7 g) thus obtained was heated under reflux in a mixture of 20 ml of alcohol and 20 ml of aqueous 10% potassium hydroxide solution for 5 hours. After cooling, the mixture was acidified by addition of hydrochloric acid, extracted with ether, the extract washed with water, dried over anhydrous sodium sulfate, and the solvent evaporated to give an oily substance, which was subjected to vacuum distillation affording 1.3 g of the desired compound, b.p. 190°–195° C. at 0.3 mm Hg (bath temp.). The compound solidified as it was cooled to crystals, m.p. 71.5°–72.5° C.

Elementary analysis for $C_{15}H_{18}O_3$ Calculated: C, 73.14; H, 7.37. Found: C, 73.09; H, 7.40.

EXAMPLE 5

2-[4-(2-Oxocyclopentan-1-ylmethyl)phenyl]-propionic Acid L-Arginine Salt

To a solution of 1.23 g of 2-[4-(2-oxocyclopentan-1-ylmethyl)phenyl]propionic acid in a mixture of 1.6 ml of acetone and 0.5 ml of water was dropwise added with stirring 2 ml of water containing 0.87 g of L-arginine, the mixture was stirred for 1 hour and acetone and water were removed by distillation under reduced pressure to give 2.1 g of the desired compound, m.p. 101°–110° C.

Elementary analysis for $C_{21}H_{32}O_5N_4$ Calculated: C, 59.93; H, 7.67; N, 13.33. Found: C, 59.69; H, 7.88; N, 13.26.

EXAMPLE 6

2-[4-(2-Hydroxyiminocyclopentan-1-ylmethyl)phenyl]-propionic Acid

To a solution of 1.5 g of 2-[4-(2-oxocyclopentan-1-ylmethyl)phenyl]propionic acid in 10 ml of ethanol was added a solution of 0.43 g of hydroxylamine hydrochloride in 2 ml of water, subsequently a solution of 0.76 g of sodium hydroxide in 2 ml of water, and the mixture was heated under reflux for 3 hours. The reaction mixture was poured into an ice-water, acidified by addition of hydrochloric acid, and then extracted with ethyl acetate. The extract was washed with water, dried over anhydrous sodium sulfate, and the solvent removed by distillation to give 1.4 g of crystals of the desired compound. Recrystallization of the product from a mixture of ether-n-hexane afforded colorless crystals, m.p. 146°–148° C.

Elementary analysis for $C_{15}H_{19}O_3N$ Calculated: C, 68.94; H, 7.33; N, 5.36. Found: C, 68.83; H, 7.42; N, 5.39.

EXAMPLE 7

4-(2-Hydroxyiminocyclopentan-1-ylmethyl)phenylacetic Acid

A solution of 1.8 g of 4-(2-oxocyclopentan-1-ylmethyl)phenylacetic acid, 0.56 g of hydroxylamine hydrochloride, and 1.32 g of anhydrous sodium acetate in 20 ml of 80% ethanol was heated under reflux for 2 hours, and ethanol was then removed by distillation. The residual oily substance was poured into an ice-water, the mixture was acidified by addition of hydrochloric acid and extracted with ethyl acetate. The extract was washed with water, dried over anhydrous sodium sulfate, the solvent removed by distillation to give crystals containing an oily substance. Recrystallization of the product from a mixture of ether and n-hexane yielded 0.32 g of an oxime (isomer a), m.p. 137°–139° C.

Elementary analysis for $C_{14}H_{17}O_3N$ Calculated: C, 67.99; H, 6.93; N, 5.66. Found: C, 67.81; H, 6.78; N, 5.61.

The residue obtained by concentration of the mother liquor was recrystallized from a mixture of ether and n-hexane to afford 0.03 g of an oxime (isomer b), m.p. 152°–155° C.

Elementary analysis for $C_{14}H_{17}O_3N$ Calculated: C, 67.99; H, 6.93; N, 5.66. Found: C, 68.05; H, 6.80; N, 5.72.

EXAMPLE 8

2-[4-(2-Hydroxyiminocyclohexan-1-ylmethyl)phenyl]-propionic Acid

A solution of 1.3 g of 2-[4-(2-oxocyclohexan-1-ylmethyl)phenyl]propionic acid, 0.33 g of hydroxylamine hydrochloride and 1.6 g of sodium acetate trihydrate in 85% ethanol was heated with stirring at 70°–75° C. for 2 hours, and the mixture was poured into 100 ml of water and extracted with ether. The extract was washed with water, dried over anhydrous sodium sulfate, and the solvent removed by distillation to give 1.4 g of the desired compound, which by recrystallization from a mixture of ethyl acetate and n-hexane afforded colorless prisms, m.p. 143°–150.5° C.

Elementary analysis for $C_{16}H_{21}O_3N$ Calculated: C, 69.79; H, 7.69; N, 5.09. Found: C, 69.42; H, 7.67; N, 4.97.

EXAMPLE 9

4-(2-Hydroxyiminocyclohexan-1-ylmethyl)phenylacetic Acid

A solution of 0.64 g of 4-(2-oxocyclohexan-1-ylmethyl)phenylacetic acid, 0.19 g of hydroxylamine hydrochloride, and 0.45 g of anhydrous sodium acetate in 10 ml of 80% ethanol was heated under reflux for 2 hours. The solvent was removed by distillation, water and ethyl acetate were added to the residue, the mixture was acidified by addition of diluted hydrochloric acid, the ethyl acetate layer separated and the water layer was then extracted with ethyl acetate. The extract was washed with water, dried over anhydrous sodium sulfate, the solvent removed by distillation to give 0.7 g of the desired compound, which by recrystallization from ethyl acetate afforded colorless crystals, m.p. 180°–184° C.

Elementary analysis for $C_{15}H_{19}O_3N$ Calculated: C, 68.94; H, 7.33; N, 5.36. Found: C, 68.81; H, 7.30; N, 5.41.

EXAMPLE 10

2-[4-(2-Hydroxyiminocyclopentan-1-ylmethyl)phenyl]propionic Acid L-Arginine Salt To a solution of 0.87 g of 2-[4-(2-hydroxyiminocyclopentan-1-ylmethyl)phenyl]propionic acid in 10 ml of acetone were added 5 ml of water and subsequently a solution of 0.58 g of L-arginine in 10 ml of water, and the mixture was allowed to stand for 1 hour. To the reaction mixture was then added 10 ml of acetone and allowed to stand affording 1.4 g of the desired compound as colorless prisms, m.p. 193°–196° C. (decomp.).

Elementary analysis for $C_{21}H_{33}O_5N_5$ Calculated: C, 57.91; H, 7.64; N, 16.08. Found: C, 57.67; H, 7.61; N, 15.98.

EXAMPLE 11

2-[4-(2-Hydroxyiminocyclopentan-1-ylmethyl)phenyl]propionic Acid

To a solution of 2.0 g of hydroxyiminocyclopentane in 30 ml of tetrahydrofuran was added 28 ml of 15% n-hexane solution of n-butyllithium at room temperature. After the mixture was stirred for 30 minutes at the same temperature, a solution of 6.0 g of ethyl 2-(4-iodomethylphenyl)propionate in 20 ml of tetrahydrofuran was added and stirring was continued for further 10 minutes at room temperature. The reaction mixture was poured into a mixture of 80 ml of ice-water and 20 ml of concentrated hydrochloric acid, extracted with ether, the solvent removed by distillation to afford a residue, to which 1.0 g of sodium hydroxide and 40 ml of methanol were added and the mixture was allowed to stand at room temperature overnight. To the reaction mixture was added 30 ml of water, methanol was removed by distillation, and the residual aqueous layer was shaken with ether and then acidified with hydrochloric acid. Extraction of the acidified layer with ether and decoloration of the product through a silica gel column afforded 2.8 g of the desired compound, which by recrystallization from a mixture of ether and n-hexane yielded colorless crystals, m.p. 146°–148° C.

Elementary analysis for $C_{15}H_{19}O_3N$ Calculated: C, 68.94; H, 7.33; N, 5.36. Found: C, 69.13; H, 7.20; N, 5.14.

EXAMPLE 12

Ethyl 2-[4-(2-Hydroxyiminocyclohexan-1-ylmethyl)phenyl]propionate

To a solution of 3.95 g of hydroxyiminocyclohexane in 40 ml of tetrahydrofuran was added 45 ml of 15% n-hexane solution of n-butyllithium at room temperature. After the mixture was stirred for 30 minutes at the same temperature, a solution of 9.4 g of ethyl 2-(4-iodomethylphenyl)propionate in 30 ml of tetrahydrofuran was added and stirring was continued for further 1 hour at room temperature. The reaction mixture was poured into a mixture of 100 ml of ice-water and 20 ml of concentrated hydrochloric acid, and extracted with ether. The product thus obtained was purified through a chromatography on a column of silica gel [eluent: ethyl acetate — methylene chloride (1:3)] to afford 1.0 g of the starting compound recovered and 4.5 g of the desired compound, which by recrystallization from a mixture of ether and n-hexane yielded colorless crystals, m.p. 102°–104° C.

Elementary analysis for $C_{18}H_{25}O_3N$ Calculated: C, 71.25; H, 8.31; N, 4.62. Found: C, 71.00; H, 8.09; N, 4.51.

EXAMPLE 13

2-[4-(2-Hydroxyiminocyclohexan-1-ylmethyl)phenyl]propionic Acid

Three grams of ethyl 2-[4-(2-hydroxyiminocyclohexan-1-ylmethyl)phenyl]propionate and 0.8 g of sodium hydroxide were dissolved in 50 ml of methanol and the solution was allowed to stand at room temperature overnight. To the reaction mixture was added 20 ml of water, methanol was removed by distillation and the residue was acidified with hydrochloric acid to precipitate crystals, which were collected by filtration and recrystallized from a mixture of ether and n-hexane affording 2.1 g of colorless crystals, m.p. 148°–150° C.

Elementary analysis for $C_{16}H_{21}O_3N$ Calculated: C, 69.79; H, 7.69; N, 5.09. Found: C, 69.51; H, 7.39; N, 4.82.

Referential Example 1.

Ethyl 2-[4-(1-Ethoxycarbonyl-2-oxocyclopentan-1-ylmethyl)phenyl]propionate

To 200 ml of dimethyl formamide containing 6.0 g of potassium hydroxide was added 15.6 g of 2-carboethoxycyclopentanone with stirring at room temperature to give a homogeneous solution. Under ice-cooling, 25 g of ethyl 2-(p-chloromethylphenyl)propionate was added dropwise thereto, and the mixture was heated at 80° C. with stirring for 2 hours. After completion of the reaction, the reaction mixture was poured into an ice-water, extracted with ether, the extract washed with water, dried over anhydrous sodium sulfate, and the solvent removed by distillation to give 28 g of an oily substance, which was subjected to a vacuum distillation affording 21 g of the desired compound, b.p. 175°–178° C. at 0.5 mm Hg.

Elementary analysis for $C_{20}H_{26}O_5$ Calculated: C, 69.34; H, 7.57. Found: C, 69.10; H, 7.20.

Referential Example 2

Ethyl 2-[4-(1-Ethoxycarbonyl-2-oxocyclohexan-1-ylmethyl)-phenyl]propionate

To a mixture of 9.6 g of 50% sodium hydride and 200 ml of dimethyl formamide was added dropwise 34 g of ethyl 2-cyclohexanone carboxylate under ice-cooling, the mixture was stirred at 50° C. for 30 minutes, thereafter again under ice-cooling 45.3 g of ethyl 2-(p-chloromethylphenyl)propionate was added dropwise, and the mixture was heated at 50°–60° C. with stirring for 1 hour. After the reaction was completed, the reaction mixture was poured into an ice-water, extracted with ether, the extract washed with water, dried over anhydrous sodium sulfate, and the solvent removed by distillation to give 69.5 g of an oily substance, which was subjected to a vacuum distillation affording 57 g of the desired compound as a colorless oily substance, b.p. 200°–205° C. at 0.4 mm Hg.

Elementary analysis for $C_{21}H_{28}O_5$ Calculated: C, 69.97; H, 7.83. Found: C, 69.85; H, 7.78.

Referential Example 3

Ethyl 2-[4-(1-Ethoxycarbonyl-2-oxocyclopentan-1-ylmethyl)-phenyl]acetate

A mixture of 9.4 g of ethyl 2-cyclopentanonecarboxylate, 10.6 g of ethyl p-chloromethylphenylacetate, 3.58 g of potassium hydroxide and 60 ml of dimethyl formamide was stirred at room temperature for 5 hours, at 50° C. for 1 hour and thereafter at room temperature overnight. The reaction mixture was acidified by addition of acetic acid, dimethyl formamide was removed by distillation, water was added to the residue, and the mixture was extracted with ether. The extract was washed with water, dried over anhydrous sodium sulfate, and the solvent evaporated to give an oily substance, which was subjected to a vacuum distillation affording 12 g of the desired compound, b.p. 180°–190° C. at 0.8 mm Hg.

Elementary Analysis for $C_{19}H_{24}O_5$ Calculated: C, 68.65; H, 7.28. Found: C, 68.41; H, 7.33.

Referential Example 4

Ethyl 2-(4-Iodomethylphenyl)propionate

After a solution of 15 g of sodium iodide in 140 ml of methyl ethyl ketone was refluxed for 1 hour, 12.5 g of ethyl 2-(4-chloromethylphenyl)propionate was added and refluxing was continued for further 8 hours. After the reaction was completed, methyl ethyl ketone was removed by distillation from the reaction mixture under reduced pressure, the residue was poured into ice-water and extracted with ether. The extract was washed with water and an aqueous sodium thiosulfate solution, successively, dried, and the solvent was evaporated to give 16.3 g of the desired compound as an oily and slightly yellow substance.

Elementary analysis for $C_{12}H_{15}O_2I$ Calculated: C, 45.30; H, 4.75. Found: C, 45.12; H, 4.47.

What is claimed is:

1. A compound having the formula

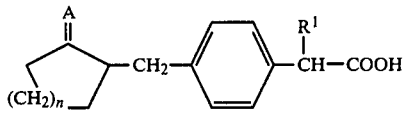

wherein $R^1$ represents hydrogen atom or a lower alkyl group, A represents oxo group or hydroxyimino group, n is an integer from 1 to 3 and a nontoxic pharmaceutically acceptable salt thereof.

2. A compound of claim 1 wherein $R^1$ is hydrogen atom or methyl group.

3. A compound of claim 1 wherein $R^1$ is hydrogen atom.

4. A compound of claim 1 wherein $R^1$ is methyl group.

5. A compound of claim 1 wherein n is 1 or 2.

6. A compound of claim 1 wherein $R^1$ is hydrogen atom or methyl group and n is 1 or 2.

7. A compound of claim 1 wherein $R^1$ is hydrogen atom and n is 1 or 2.

8. A compound of claim 1 wherein $R^1$ is methyl group and n is 1 or 2.

9. The compound of claim 1 which is 4-(2-oxocyclopentan-1-ylmethyl)phenylacetic acid.

10. The compound of claim 1 which is 4-(2-oxocyclohexan-1-ylmethyl)phenylacetic acid.

11. The compound of claim 1 which is 2-[4-(2-oxocyclopentan-1-ylmethyl)phenyl]propionic acid.

12. The compound of claim 1 which is 2-[4-(2-oxocyclohexan-1-ylmethyl)phenyl]propionic acid.

13. The compound of claim 1 which is 4-(2-hydroxyiminocyclopentan-1-ylmethyl)phenylacetic acid.

14. The compound of claim 1 which is 4-(2-hydroxyiminocyclohexan-1-ylmethyl)phenylacetic acid.

15. The compound of claim 1 which is 2-[4-(2-hydroxyiminocyclopentan-1-ylmethyl)phenyl]propionic acid.

16. The compound of claim 1 which is 2-[4-(2-hydroxyiminocyclohexan-1-ylmethyl)phenyl]propionic acid.

17. The compound of claim 1 which is 2-[4-(2-oxocyclopentan-1-ylmethyl)phenyl]propionic acid L-arginine salt.

18. The compound of claim 1 which is 2-[4-(2-oxocyclohexan-1-ylmethyl)phenyl]propionic acid L-arginine salt.

19. The compound of claim 1 which is 2-[4-(2-hydroxyiminocyclopentan-1-ylmethyl)phenyl]propionic acid L-arginine salt.

20. The compound of claim 1 which is 2-[4-(2-hydroxyiminocyclohexan-1-ylmethyl)phenyl]propionic acid L-arginine salt.

21. A pharmaceutical composition for treating inflammation in mammals comprising an inert pharmaceutically acceptable carrier and an anti-inflammatory effective amount of a compound of claim 1 or a nontoxic pharmaceutically acceptable salt of said compound.

22. The composition of claim 21, containing said salt, wherein said salt is selected from the group consisting of a sodium salt, a calcium salt, an aluminum salt, a lysine salt and an arginine salt.

23. The composition of claim 22, wherein said salt is a salt of 4-(2-oxocyclopentan-1-ylmethyl)phenylacetic acid.

24. The composition of claim 22, wherein said salt is a salt of 4-(2-oxocyclohexan-1-ylmethyl)phenylacetic acid.

25. The composition of claim 22, wherein said salt is a salt of 2-(4-(2-oxocyclopentan-1-ylmethyl)phenyl)propionic acid.

26. The composition of claim 22, wherein said salt is a salt of 2-(4-(2-oxocyclohexan-1-ylmethyl)phenyl)propionic acid.

27. The composition of claim 22, wherein said salt is a salt of 4-(2-hydroxyiminocyclopentan-1-ylmethyl)-phenylacetic acid.

28. The composition of claim 22, wherein said salt is a salt of 4-(2-hydroxyiminocyclohexan-1-ylmethyl)-phenylacetic acid.

29. The composition of claim 22, wherein said salt is a salt of 2-(4-(2-hydroxyiminocyclopentan-1-ylmethyl)-phenyl)propionic acid.

30. The composition of claim 22, wherein said salt is a salt of 2-(4-(2-hydroxyiminocyclohexan-1-ylmethyl)-phenyl)propionic acid.

31. The non-toxic pharmaceutically acceptable salt of the compound of claim 1, wherein said salt is selected from the group consisting of a sodium salt, a calcium salt and an aluminum salt.

32. The salt of claim 31, wherein said salt is a salt of 2-(4-(2-oxocyclopentan-1-ylmethyl)phenyl)propionic acid.

* * * * *